United States Patent
Kaiser et al.

(10) Patent No.: US 8,942,804 B2
(45) Date of Patent: Jan. 27, 2015

(54) MECHANISM FOR DETECTING CORONARY ISCHEMIA

(71) Applicants: Clayton A. Kaiser, Mountain View, CA (US); Daniel W. Kaiser, Nashville, TN (US)

(72) Inventors: Clayton A. Kaiser, Mountain View, CA (US); Daniel W. Kaiser, Nashville, TN (US)

(*) Notice: Subject to any disclaimer, the term of this patent is extended or adjusted under 35 U.S.C. 154(b) by 0 days.

(21) Appl. No.: 13/652,234

(22) Filed: Oct. 15, 2012

(65) Prior Publication Data

US 2014/0107722 A1 Apr. 17, 2014

(51) Int. Cl.
*A61N 1/365* (2006.01)

(52) U.S. Cl.
CPC .................................... *A61N 1/365* (2013.01)
USPC .......................................................... 607/17

(58) Field of Classification Search
USPC .................... 607/9–11, 17–18; 600/508–509
See application file for complete search history.

(56) References Cited

U.S. PATENT DOCUMENTS

| | | | |
|---|---|---|---|
| 5,199,428 A | 4/1993 | Obel et al. | |
| 6,645,153 B2 | 11/2003 | Kroll et al. | |
| 6,738,674 B2 | 5/2004 | Osypka | |
| 6,892,095 B2 | 5/2005 | Salo | |
| 6,915,149 B2 | 7/2005 | Ben-Haim | |
| 7,058,443 B2 | 6/2006 | Struble | |
| 7,103,412 B1 | 9/2006 | Kroll | |
| 7,164,948 B2 | 1/2007 | Struble et al. | |
| 7,181,269 B1 | 2/2007 | Kroll | |
| 7,218,960 B1 | 5/2007 | Min et al. | |
| 7,277,761 B2 | 10/2007 | Shelchuk | |
| 7,366,568 B2 | 4/2008 | Pastore et al. | |
| 7,515,969 B2 | 4/2009 | Tockman et al. | |
| 7,610,086 B1 | 10/2009 | Ke et al. | |
| 7,660,616 B1 | 2/2010 | Poore | |
| 7,769,451 B2 | 8/2010 | Yang et al. | |
| 7,844,333 B1 | 11/2010 | Koh et al. | |
| 2005/0004476 A1 | 1/2005 | Payvar et al. | |
| 2006/0247702 A1* | 11/2006 | Stegemann et al. | 607/17 |
| 2009/0024194 A1* | 1/2009 | Arcot-Krishnamurthy et al. | 607/113 |
| 2009/0099467 A1 | 4/2009 | Toren-Herrinton et al. | |
| 2009/0318989 A1 | 12/2009 | Tomaschko et al. | |
| 2010/0185252 A1 | 7/2010 | Björling et al. | |
| 2011/0066017 A1 | 3/2011 | Kuhn | |
| 2011/0082350 A1 | 4/2011 | Koh | |
| 2011/0106201 A1 | 5/2011 | Bhunia | |
| 2011/0144711 A1 | 6/2011 | Bornzin et al. | |
| 2012/0108991 A1* | 5/2012 | Song et al. | 600/509 |

OTHER PUBLICATIONS

Crake et al.; Continuous recording of coronary sinus oxygen saturation during atrial pacing in patients with coronary artery disease or with syndrome X; Br Heart J; 59(1):31-38; Jan. 1988.

(Continued)

*Primary Examiner* — Rex R Holmes
(74) *Attorney, Agent, or Firm* — Shay Glenn LLP

(57) ABSTRACT

A system for detecting myocardial ischemia includes an implantable device having one or more leads connected thereto, at least one electrode on a lead of the device, and a microprocessor in the implantable device. The electrode is configured to stimulate the heart. The at least one sensor is configured to measure a characteristic of blood in a coronary vessel. The microprocessor is programmed to: run a stress test on the heart by stimulating the heart with the electrode; record data obtained from the at least one sensor during the stress test; and determine whether there is myocardial ischemia based upon the recorded data.

15 Claims, 8 Drawing Sheets

(56) References Cited

OTHER PUBLICATIONS

Kupper et al; Measurement of regional and global coronary sinus blood flow with the continuous thermodilution technique. II. Clinical studies in patients with coronary heart disease (author's transl); Z Kardiol; 70(2):116-123; Feb. 1981 (German wEng Abs.).

Kikuchi et al.; Continuous measurement of coronary sinus oxygen saturation in patients with effort angina and vasospastic angina; J Cardiol; 21(4):857-868; (year of pub. sufficiently earlier than effective US filing date and any foreign priority date) 1991 (Japanese wEngAbs).

Nitenberg et al.; Coronary vascular reserve in humans: a critical review of methods of evaluation and of interpretation of the results; Eur heart J, 16(Suppl I):7-21; Aug. 1995.

* cited by examiner

MECHANISM FOR DETECTING CORONARY ISCHEMIA

INCORPORATION BY REFERENCE

All publications and patent applications mentioned in this specification are herein incorporated by reference to the same extent as if each individual publication or patent application was specifically and individually indicated to be incorporated by reference.

BACKGROUND

Coronary ischemia is a disease caused by the reduction in blood flow in the coronary arteries. Some forms of coronary ischemia are particularly severe, leading to acute coronary syndrome (ACS), which is a dangerous condition often caused by the rupture of plaque in the arteries which leads to an obstruction to the blood flow down the artery. Other forms of coronary ischemia are more chronic, in which the coronary artery gradually narrows over time from atherosclerosis, causing the blood flow down the coronary artery to slowly decrease. This type of ischemia is often less dangerous to the patient, as the heart is able to compensate by creating collateral arteries.

Nationwide, more than 6 million emergency department (ED) visits a year involve patients presenting with chest pain, accounting for more than 5% of all ED visits. Many of these patients are admitted to the hospital for signs of ACS. However, more than 60% of the patients admitted to the hospital with chest pain do not have acute coronary syndrome ACS.

Despite the over-triage of patients (with economic implications of over $8 billion in annual costs), the rate of missed diagnoses of hospitalized patients with ACS remains unacceptably high (2% to 8%) with concordant serious public health consequences. Indeed, the significant morbidity and mortality associated with missing a myocardial infarction is the highest overall cost to insurers of any missed diagnosis in emergency medicine.

Furthermore, there is no simple established test for validating whether a person with chest pain has a low enough risk of ACS to be discharged from the hospital. Rather, patients deemed to be at increased risk are subjected to a variety of non-invasive tests including exercise treadmill testing, nuclear scintigraphy, coronary computed tomography angiography (CTA), or a myocardial perfusion single photo emission computed tomography (SPECT) test.

Virtually all of these non-invasive tests involve stressing the heart, such as by infusing drugs such as adenosine or dobutamine, to determine how well the heart is being perfused by the coronary arteries. Stressing the heart can be advantageous in detecting ischemia because the coronary blood flow has to increase to the myocardium in order for the heart to work harder during the test. The increase in blood flow helps identify smaller defects in perfusion, i.e., helps increase the sensitivity or accuracy of the non-invasive test.

All of the current non-invasive stress tests involve significant time and expense. The most common non-invasive test ordered to rule on coronary ischemia, for example, is the SPECT test, which costs about $3,000 per test. Another common stress test, treadmill testing, requires a patient to run or walk on a treadmill while having sensors connected on various locations the patient's chest, involving significant time and energy for the patient. Further, current non-invasive tests are limited in their ability to detect certain types of arterial blockages, such as those caused by microvascular disease.

Over the last decade, the technique of placing a catheter lead into the coronary sinus for pacing (sometimes called cardiac resynchronization therapy or CRT) with an implantable cardioverter-defibrillator (ICD), i.e. a type of pacemaker that includes leads in both the right ventricle, the right atrial, and the coronary sinus, has become a standard of care in patients with symptoms of heart failure and a wide QRS, the ventricular component of an EKG. Indeed, the US ICD Registry Program estimates that approximately 10,000 ICD implants are placed into patients each month in the United States. Further, approximately 40% of the patients receiving ICDs are candidates for CRT (i.e. for having a lead placed in the coronary sinus). The leading cause of dilated hearts with widened QRSs is coronary ischemia.

Accordingly, a simple and cost effective mechanism for effectively detecting coronary ischemia, particularly for those patients with ICDs who are candidates for CRT therapy, is desired.

SUMMARY OF THE DISCLOSURE

The present invention relates a system for detecting myocardial ischemia including an implantable device having one or more leads connected thereto, at least one electrode on a lead of the device, and a microprocessor in the implantable device. The electrode is configured to stimulate the heart. The at least one sensor is configured to measure a characteristic of blood in a coronary vessel. The microprocessor is programmed to: (1) run a stress test on the heart by stimulating the heart with the electrode; (2) record data obtained from the at least one sensor during the stress test; and (3) determine whether there is myocardial ischemia based upon the recorded data.

This and other embodiments can include one or more of the following features. The sensors can be an oximetry sensor. The microprocessor can be configured to determine whether there is myocardial ischemia by determining whether data recorded from the sensor during the stress test has exceeded a threshold value. The microprocessor can be further configured to establish a baseline from the recorded data and set the threshold using the baseline. The system can further include an alarm connected to the implantable device and configured to transmit a warning signal if myocardial ischemia is detected. The implantable device can be a pacemaker or defibrillator. There can be at least two sensors. The microprocessor can be further programmed to determine a location of myocardial ischemia based upon a difference in the characteristic measured at the at least two sensors. The system can further include a heating or cooling element on the lead. The sensor can be a voltage sensor.

In general, in one aspect, a method of detecting myocardial ischemia includes: measuring a characteristic of blood in a coronary vessel with a sensor on a lead of an implantable device; recording data obtained from the sensor in a memory of the implantable device to establish a baseline; performing a stress test with the implantable device; measuring the characteristic with the sensor during the stress test; and comparing the characteristic measured during the stress test with the baseline to detect whether there is myocardial ischemia.

This and other embodiments can include one or more of the following features. Performing a stress test can include pacing the heart with an electrode coupled to the device at a rate of at least 100 beats per minute. Performing the stress test can include pacing the heart at a first rate for a set period of time and then, if no ischemia has been detected, increasing the rate of pacing. The method can further include stopping the stress test if the pacing rate is greater than a predetermined amount and no ischemia has been detected. There can be at least two sensors on the lead, and the method can further include determining a location of a detected myocardial ischemia by comparing the measured characteristic at the at least two sensors. The method can further include placing the at least two sensors at predetermined locations in the coronary vessel that are proximate to branches in the vessel. The characteristic can be temperature, and the method can further including heading blood in the coronary vessel using a heating or cooling element on the lead and comparing the measured temperature at the at least two sensors. The characteristic can be oxygen saturation. The characteristic can be voltage. The coronary vessel can be the coronary sinus, and the method can further include implanting the lead in the coronary sinus. The method can further include placing the sensor at a proximal end of the coronary sinus. The method can further include continuing to measure the characteristic and record data from the sensor after the stress test has been performed.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
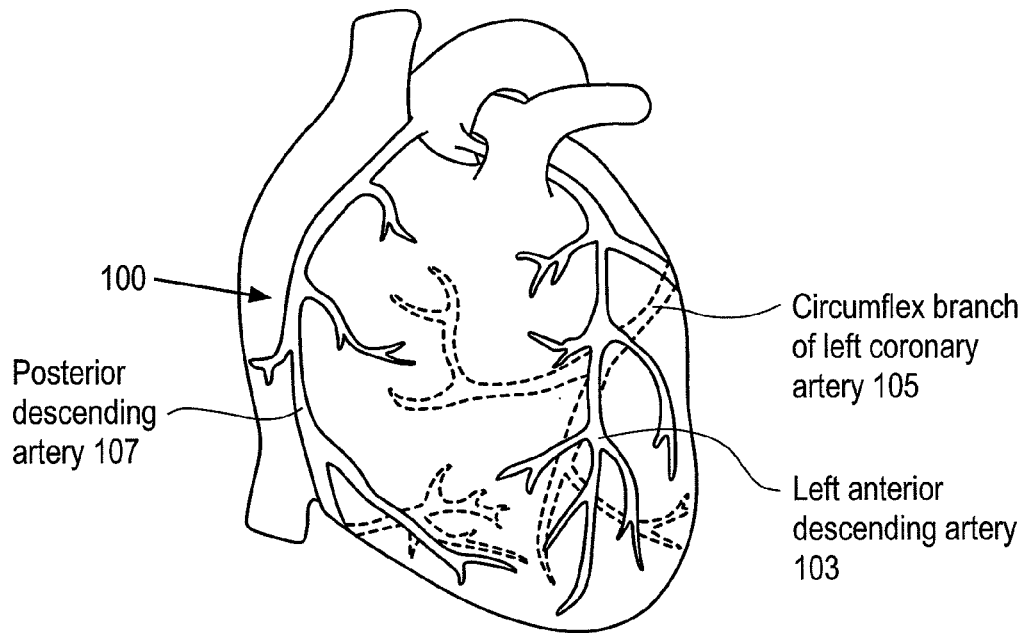
FIG. 1A is a diagram of the heart and the coronary arteries.
Figure 1B:
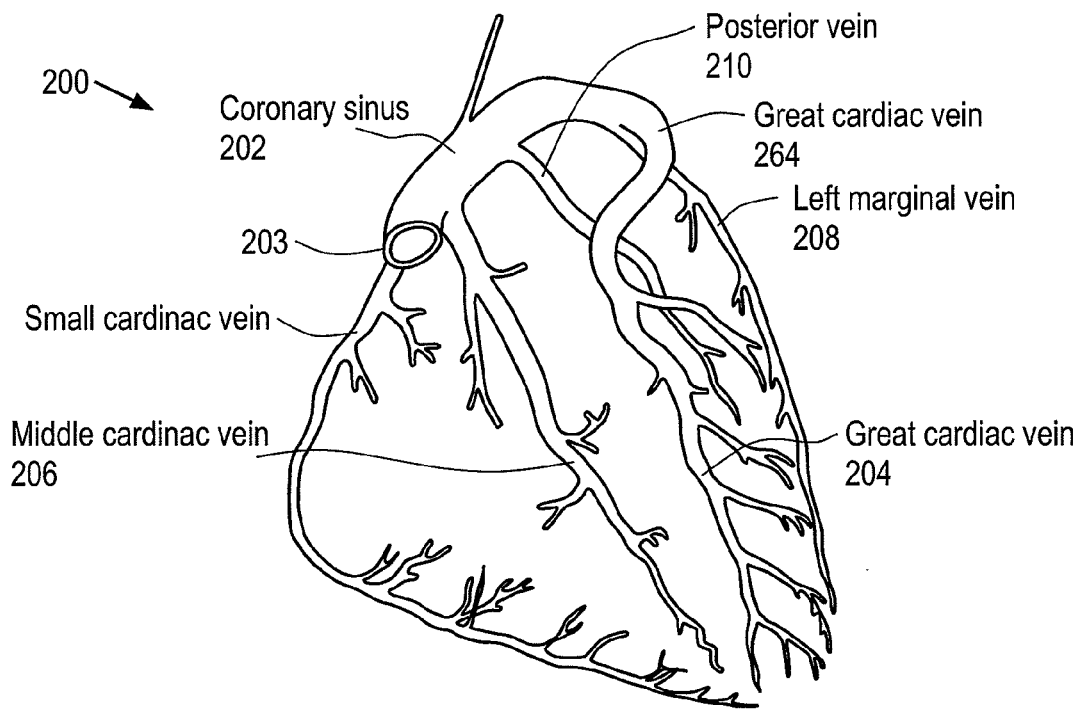
FIG. 1B is a diagram showing the cardiac veins.

Referring to FIGS. 1A and 1B, the venous drainage of the heart is variable, but generally the cardiac veins 200 follow the anatomical course of the coronary arteries 100. The great cardiac vein 204 parallels the left anterior descending artery 103 in the left anterior interventricular groove. The great cardiac vein 204 then enters the left atrioventricular groove and runs parallel with the left circumflex coronary artery 105. Here, the left marginal vein 208 and posterior vein 210 of the left ventricle 322 (see FIG. 3) join the great cardiac vein 204, which extends into the coronary sinus 202. The middle cardiac vein 206 runs parallel to the posterior descending artery 107 and also joins with the coronary sinus 202. The coronary sinus ends at the coronary sinus os 203, where it empties into the right atrium 321 (see FIG. 3). It is estimated that at least 80% of coronary blood flow is drained through the coronary sinus 202.

The coronary veins tend to drain blood from the heart that corresponds to blood supplied by the parallel or anatomically close coronary artery. Accordingly, a diseased coronary artery may result in changes in characteristics of the blood being drained by the parallel cardiac vein. For example, because the blood in the coronary arteries drains to the heart muscle and then back to the atrium through the coronary sinus venous system, changes in coronary sinus blood flow oxygenation can correspond to progression of coronary artery disease, occlusion, or acute coronary thrombosis. Indeed, studies have found that patients with coronary artery disease had a significantly larger drop in coronary sinus oxygenation during atrial pacing, i.e. stimulating the heart via a lead in the atrium to rapidly pace the heart, than patients with no coronary artery disease. Accordingly, measuring changes in coronary sinus oxygenation, or changes in another characteristic of blood, while pacing the patient's heart at high rates can provide a mechanism for detecting coronary ischemia.

Figure 2A:
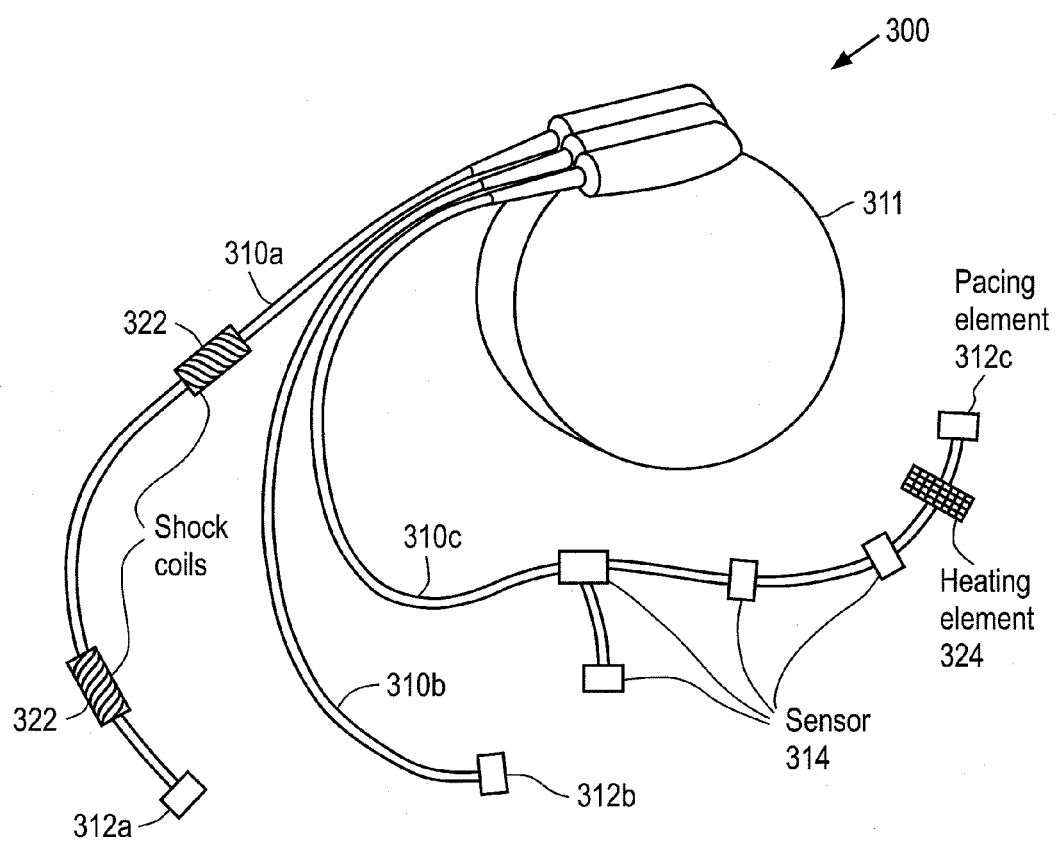
FIG. 2A is a schematic of an exemplary device for detecting coronary ischemia.
Figure 3:
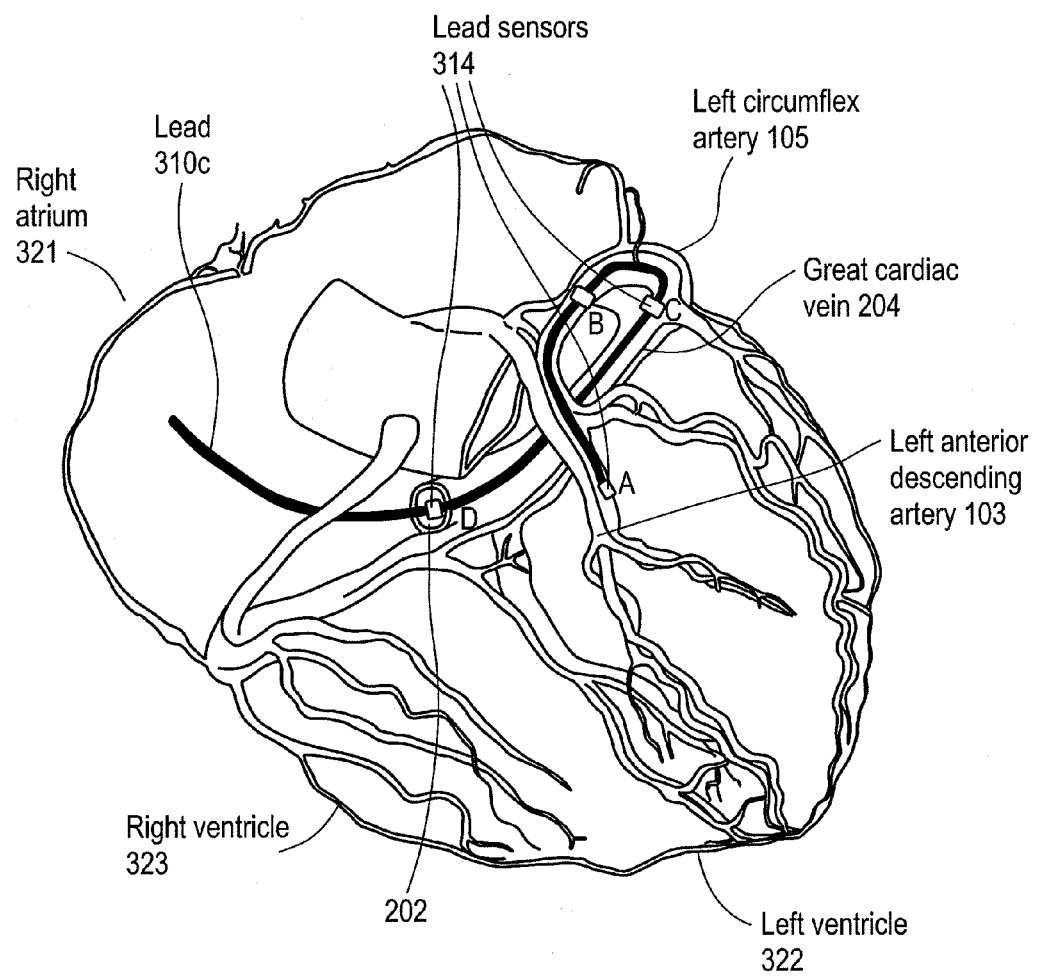
FIG. 3 is a schematic showing an exemplary placement of the leads of a device in the coronary sinus for detecting coronary ischemia in the heart.

Referring to FIG. 2A, a device 300 for detecting coronary ischemia includes a pacing device 31, such as an implantable cardiac defibrillator or pacemaker. The device 300 can further include one or more leads 310a, 310b, 310c extending from the pacing device 311. The leads 310a, 310b, 310c can include electrodes 312a, 312b, 312c thereon configured to provide energy to stimulate the heart. In the embodiment shown in FIG. 2A, there are three leads 310a, 310b, 310c. Referring to FIG. 3, using three leads can advantageously provide for biventricular pacing, as one lead can be placed in the right atrium 321, one lead can be placed in the right ventricle 323, and one lead 310c can be placed in the coronary sinus 202, similar to the set-up for standard biventricular pacing.

Referring back to FIG. 2A, one or more of the leads 310 can include one or more sensors 314 to measure characteristics of blood flow that can provide insight as to whether there is coronary ischemia. The sensors 314 can be, for example, oximetry sensors (oxygen saturation will go down during coronary ischemia), temperature sensors (the temperature will fluctuate during coronary ischemia, pH sensors (the pH will lower during coronary ischemia), sensors configured to detect troponin levels (troponin levels will rise during coronary ischemia), sensors configured to detect lactate levels (lactate levels will rise during coronary ischemia) or, sensors configured to measure hemoglobin. In another embodiment, the sensors 314 can be voltage sensors to take EKG measurements. The changes in EKG waveform can then be monitored during stress pacing to detect ischemic changes.

In some embodiments, as shown in FIG. 2A, there can be multiple sensors 314 along the length of a single lead 310c. In one embodiment, the sensors 314 can be placed at specific points along the lead 312c and/or spaced apart at specific distances such that each sensor 314 is located close to a major coronary venous branch when implanted, as described further below. Further, in some embodiments, more than one type of sensor is used, e.g., a temperature sensor and an oximetry sensor, for a single lead 310 and/or a single device 300. Although FIG. 2A shows a stimulating electrode 312 on each lead 310, there need not be. Indeed, the lead 310 including the sensors 314 may not include a stimulating electrode 312.

Further, in some embodiments, the device 300 can further include a heating or cooling element 324 on one or more of the leads 310 having sensors 314. As discussed further below, the heating or cooling element can be placed near the end of a lead to heat (or cool) blood entering the great cardiac vein, and the change in temperature can be measured with the sensors 314.

In some embodiments, one or more of the leads 310 can include one or more shock coils 322, such as on a lead that will be implanted in the right atrium. The shock coils can be used to deliver high-energy current from a generator in the device 100 if required for defibrillation.

Figure 2B:
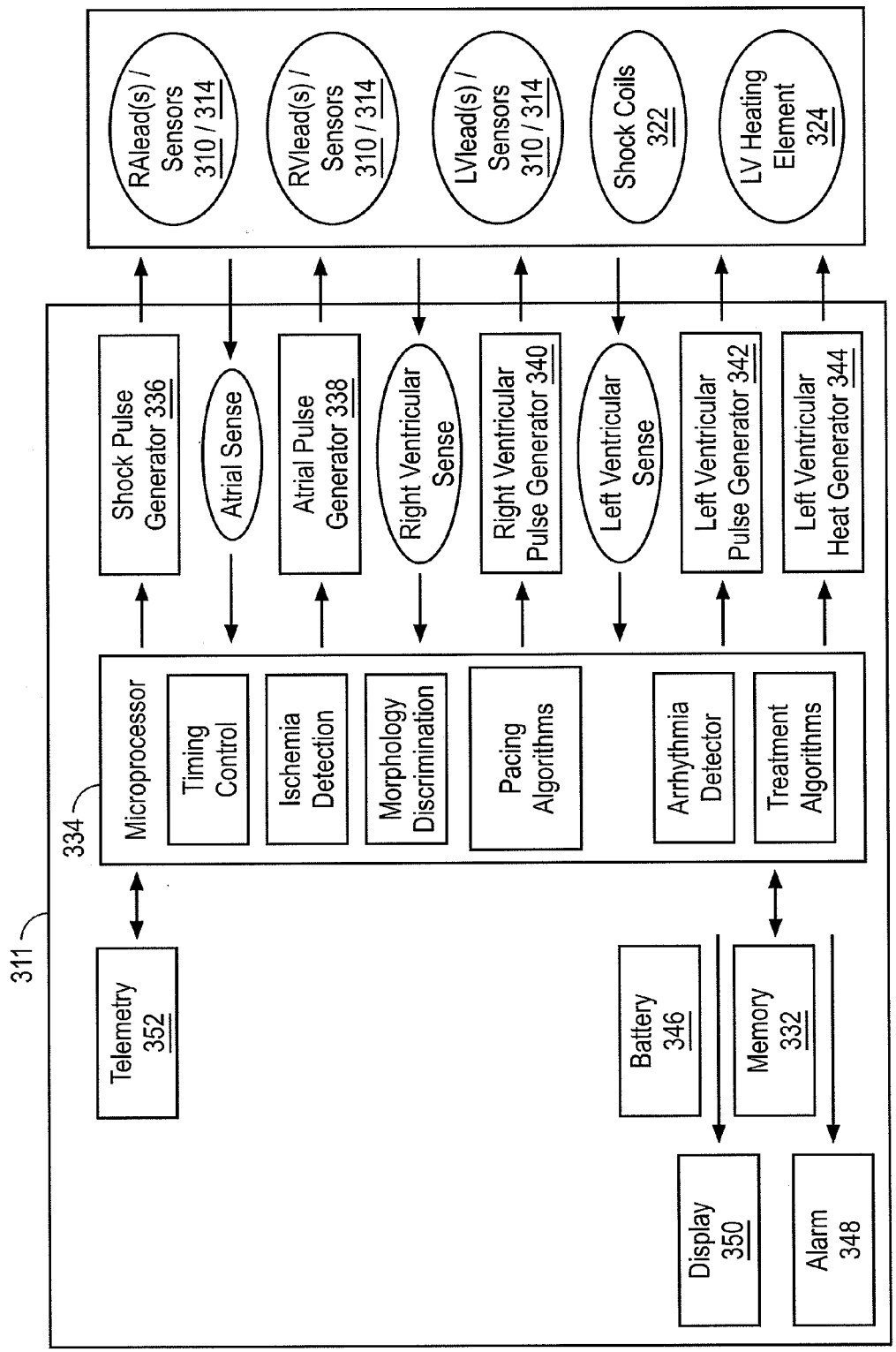
FIG. 2B is a block diagram of the device of FIG. 2A.

As shown in FIG. 2B, the pacing device 311 can include a microprocessor 334 configured to gather sensed data from the sensors, run the pacing and treatment algorithms, compile data to detect arrhythmia or ischemia, run and control timing of pacing and/or data gathering, perforin morphology discrimination, and determine whether there has been an ischemia. The pacing device 311 can further include pulse generators, such as a shock pulse generator 336 to shock the heart if necessary, an atrial pulse generator 338, a right ventricular pulse generator 340, and a left ventricular pulse generator 342. The pacing device can further include a heat generator 344, such as a register/coil of wire, that can be used to calculate coronary blood flow in combination with a temperature sensor, as described above. Further, a memory 332 capable of storing data, such as recording waveform traces from the sensors 314, can be located in the pacing device 311. Finally, the pacing device can include a power source, such as a battery 346, a display 350, an alarm 348 to indicate that ischemia has been detected, and telemetry 352 to allow external control of the pacing device 311.

Referring to FIG. 3, the device 300 can be implanted in a patient such that the lead 310c that includes the sensors 314 is placed in the coronary sinus 202. The pacing device 311 can be configured to supply energy to the heart, i.e., to pace the heart, using the electrode or electrodes on the leads 310. Further, the sensors 314 can be located within the coronary sinus so as to measure characteristic of blood in the coronary sinus that is affected by coronary ischemia. As shown in FIG. 3, in some embodiments, the sensors 314 can be positioned at locations proximate to branches in the coronary veins, such as 1-3 mm away. In one embodiment, at least one sensor 314 (for example, sensor D in FIG. 3) can be placed at the coronary sinus os. Placement of at least one sensor 314 proximate to the coronary sinus os advantageously allows for detection of characteristics of blood even from the right coronary artery, which might otherwise be overlooked due to drainage of much of the blood from the right coronary artery directly into the right ventricle through thebesian veins.

The data gathered by the device 300 can be stored in the memory of the device and accessed and/or reproduced any time that a patient's waveform trace needs to be reviewed. For example, if the patient is experiencing chest pain or undergoing a regular evaluation for coronary blockage, the data can be accessed and analyzed. Any significant deviation, such as more than approximately 30%, 20%, 15%, 10%, or 5%, could indicate coronary ischemia. Further, the deviation could advantageously demonstrate when there is viable heart muscle (and thus would benefit from PCI or surgical revascularization) or non-viable, as non-viable/scarred myocardium would be less likely to generate low coronary sinus saturations and would not benefit from revascularization.

Figure 4:
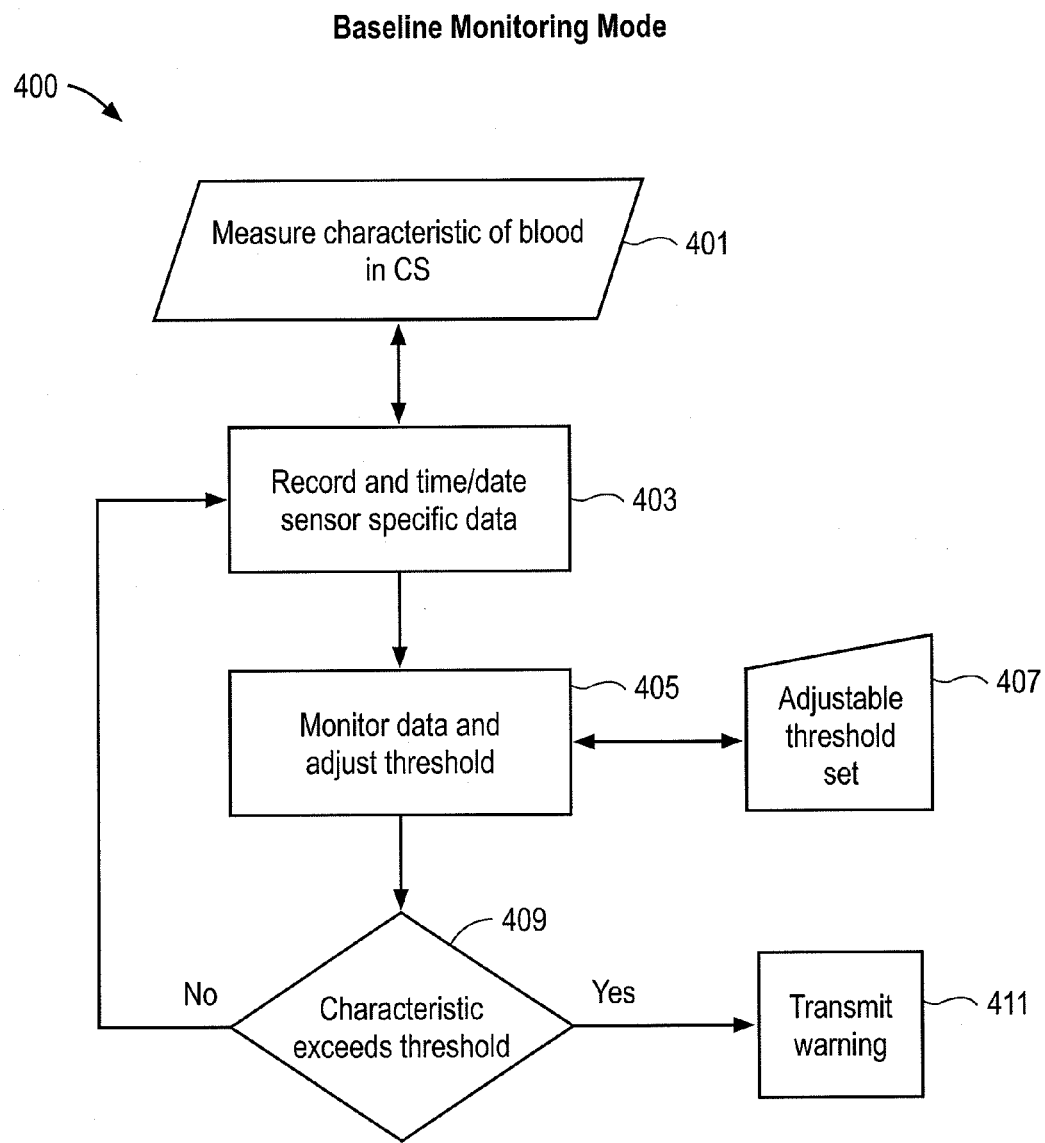
FIG. 4 is a flowchart showing use of an exemplary device for detecting coronary ischemia in baseline mode.

In one embodiment, the gathered data can be used to establish a baseline and to provide a warning if the characteristic is deviating from the baseline, i.e., if coronary ischemia is detected. An exemplary system 400 for establishing the baseline and transmitting a warning is shown in FIG. 4.

At step 401, the characteristic of blood can be gathered. In some embodiments, this collection is done through multiple sensors at multiple locations in the coronary sinus. The data can be obtained at set time intervals, such as between 1 time per second and 30 times per hour, for example 1 time per minute.

At step 403, the data can be recorded and stored. For example, the data can be recorded and stored a memory of the device. In another embodiment, the data can be transmitted to an external device and recorded and stored in the external device. The measured characteristic can be recorded as well as the data and time corresponding to the sensed data. Further, if multiple sensors are used, identifying information as to the specific sensor and location of the sensor gathered the data can be stored.

At step 407, a threshold or cutoff for the characteristic can be set. For example, the gathered data can be used to determine an average value of the characteristic for the particular patient, and the threshold can be set to be a particular deviation from the average. Thus, if oxygen saturation is being measured, the threshold can be set such that there is a drop in oxygen saturation of more than 5%, more than 10%, more than 15%, more than 20%, or more than 30% from the baseline or average value. In some embodiments, the threshold value can be set by measuring the variability of the characteristic for each individual patient, as some patients might normally run a very small range of deviations while others might have a large normal range. In some embodiments, the threshold value can be set, for example, during device implantation and initial testing, such as at about 1 standard deviation above and below the values measured during a stress test performed at device implantation.

At step 405, the data can be monitored, and the threshold value can be adjusted. That is, as more and more data is collected, a better estimate can be made as to the person's true variability on normal occasions. Accordingly, the normal variability of the characteristic can be assessed and used to readjust the error bars or percentage of deviation allowed before reaching the threshold value.

At step 409, a determination can be made as to whether the characteristic has reached or exceeded the threshold, such as whether the oxygen saturation has dropped below the threshold. This determination can be made, for example, every time that a new measurement is taken by the sensors 314.

If the characteristic has exceeded the threshold, then a warning signal can be transmitted at step 411. For example, an alarm connected to the device can sound to warn the user that the threshold has been exceeded. In another embodiment, the device can electronically transmit a warning signal that can be received at a separate location, such as a home computer or processor at a doctor's office. In some embodiments, the alarm can sound repetitively at set intervals, such as one time per 1 minute, until a particular action is taken, such as until a patient or doctor turns the alarm off. In some embodiments, there can be two warning levels—one minor level that can be turned off by a patient and one major level that can be turned off only by a physician.

If the characteristic has not exceeded the threshold, then the process can be started again at step 401.

Figure 5:
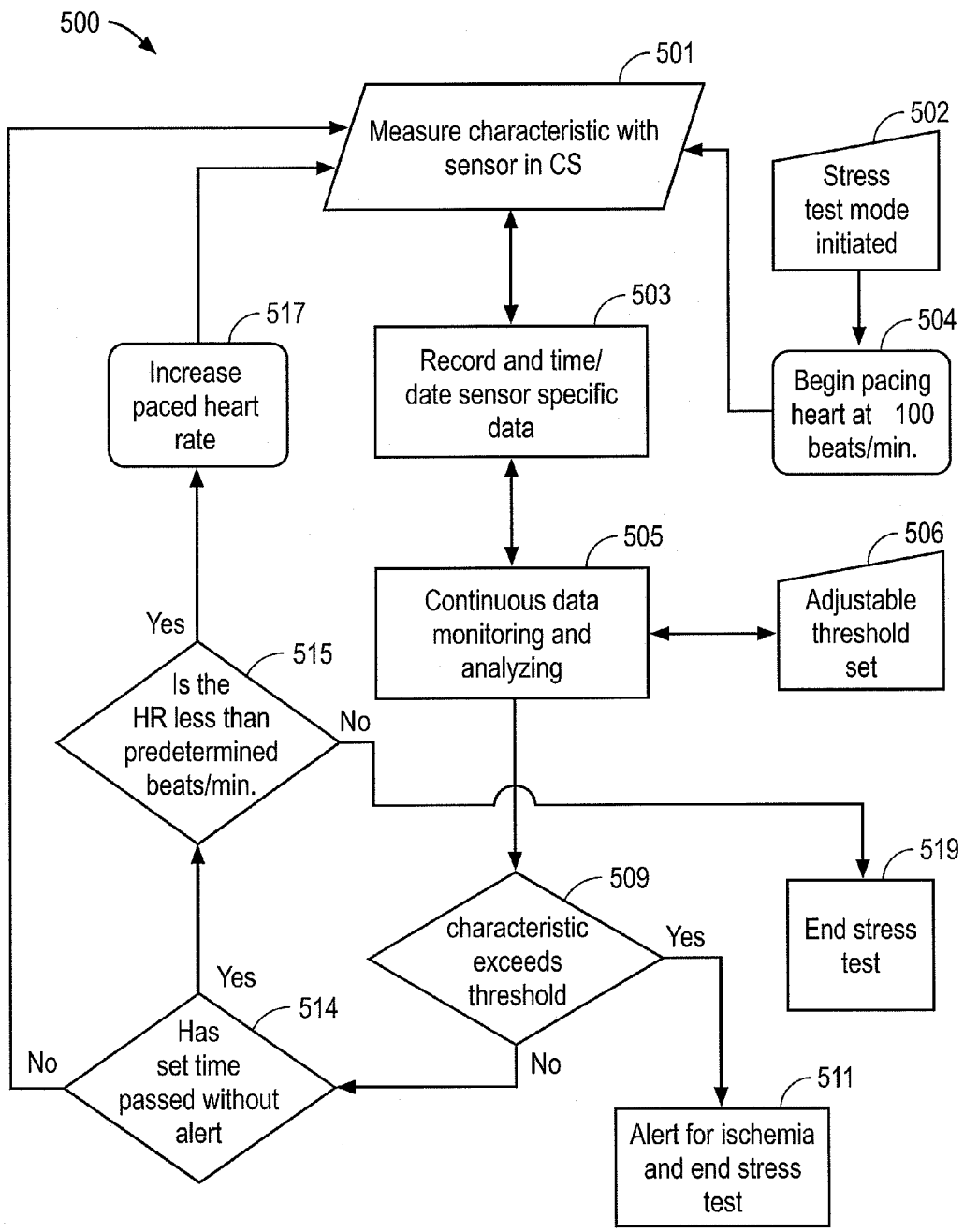
FIG. 5 is a flowchart showing use of an exemplary device for detecting coronary ischemia in stress test mode.

In one embodiment, the data can be gathered during a stress test and compared to a baseline or threshold to test for ischemia. That is, because blockages can often not be detected until the heart is stressed, the device 300 can be used to stress the test under controlled conditions and then be used to detect ischemia. An exemplary flowchart 500 for running the stress test and testing for ischemia is shown in FIG. 5.

At step 502, a stress test mode is initiated on the device. As a result, at step 504, the pacing rate of the heart is set at greater than or equal to a particular value, such as 100 beats per minute, 110 beats per minute, 120 beats per minute, or 130 beats per minute. This can be done by sending an electrical impulse through leads 310 and electrodes 312 to stimulate contraction of the heart muscle.

At step 501, a characteristic of blood can be measured, as described above with respect to step 401 of flowchart 400. At step 503, the data can be recorded and stored, as described above with respect to step 403 of flowchart 400.

At step 507, an adjustable characteristic threshold can be set. In one embodiment, this threshold can be set based upon baseline data gathered from the device itself, such as described with reference to flowchart 400.

At step 505, data gathered and recorded is continuously monitored and compared to the threshold value. At step 509, a determination is made as to whether the characteristic has reached or exceeded the threshold, as described above with respect to step 409 of flowchart 400.

If the characteristic has reached or exceeded the threshold in response to the increased pacing rate, then, at step 511, the stress test can be ended and a signal can be transmitted alerting for ischemia. For example, a warning can sound and/or data can be transmitted to a doctor demonstrating that the threshold has been exceeded. If the characteristic has not reached or exceeded the threshold value, then the characteristic can continue to be measured at step 501, recorded and step 503, and monitored at step 505.

At step 514, it can be determined whether a set time has passed without an ischemic alert. For example, it can be determined whether 1-5 minutes have passed, such as approximately 2 minutes, without an ischemic alert. If the set time has not passed, then the characteristic can continue to be measured at step 501, recorded at step 503, monitored at step 505, and evaluated at step 509. On the other hand, if the set time has passed, then it can be assumed that ischemia is not going to be detected at the set pacing rate.

Accordingly, if the set time has paced, then at step 515, it can be determined whether or not the pacing rate is under a predetermined number, such as under 180 beats per minute. If the pacing rate is not under the set pacing rate, i.e., if the pacing rate is so high that pacing would be dangerous, then the stress test can be ended at step 519. On the other hand, if the pacing rate is less than the predetermined amount, then, at step 517, the rate of pacing can be increased. For example, the pacing rate can be increased, such as increased by 5 to 40 beats per minute, for example by approximately 20 beats per minute. The increased heart rate can advantageously detect a defect more effectively, as the heart has to work harder to keep up with the fast pacing. The process can then begin again at step 501 until the stress test is either ended without discovery of an ischemia at step 519 or with an alert for ischemia and end of the stress test at step 511.

After the stress test is ended, the characteristic can continue to be measured, recorded, and/or analyzed. For example, the device 300 can be run in baseline mode as described with respect to flowchart 400.

Figure 6A:
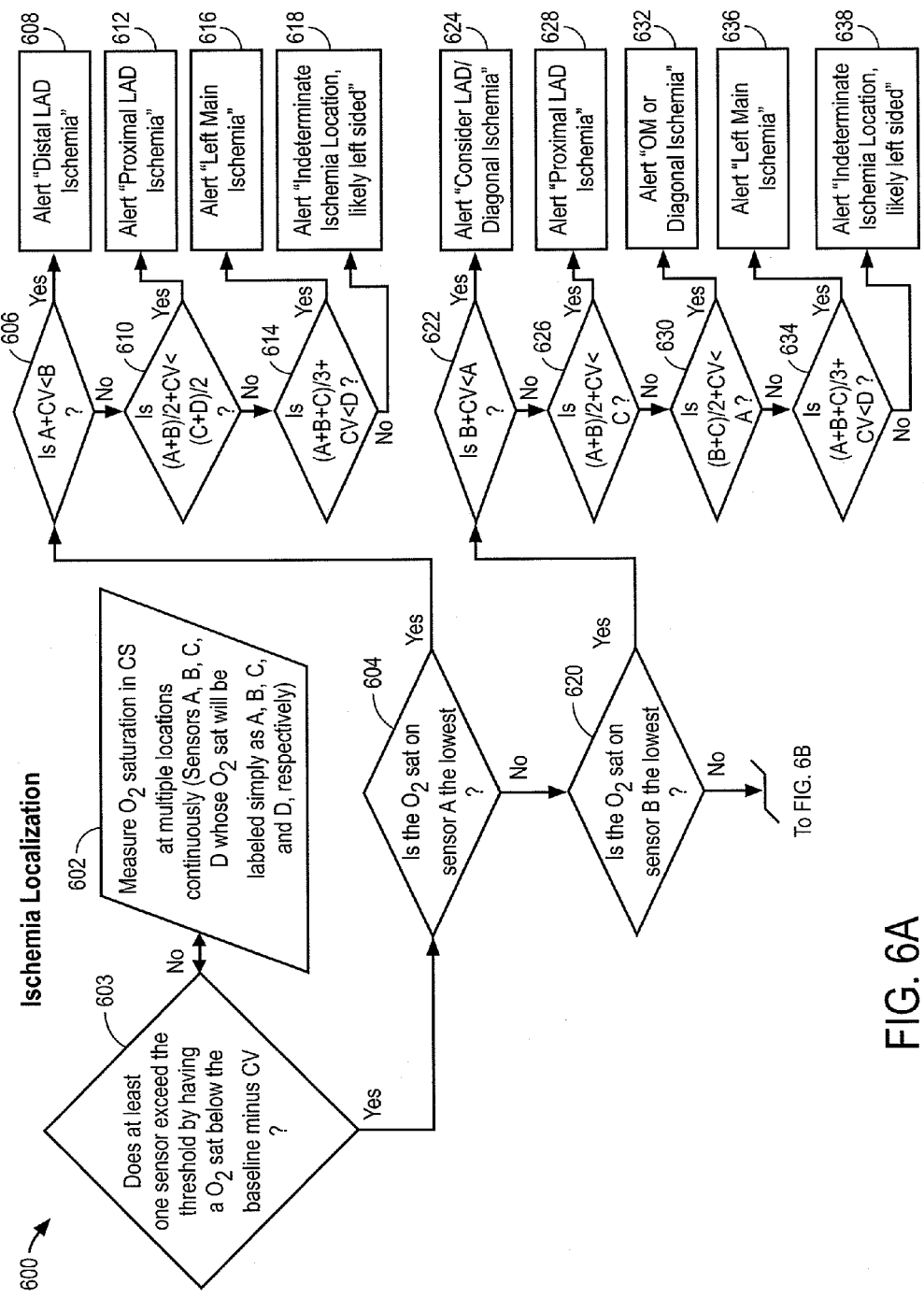
FIGS. 6A and 6B are a flowchart showing use of an exemplary device to determine a location of coronary ischemia.
Figure 6B:
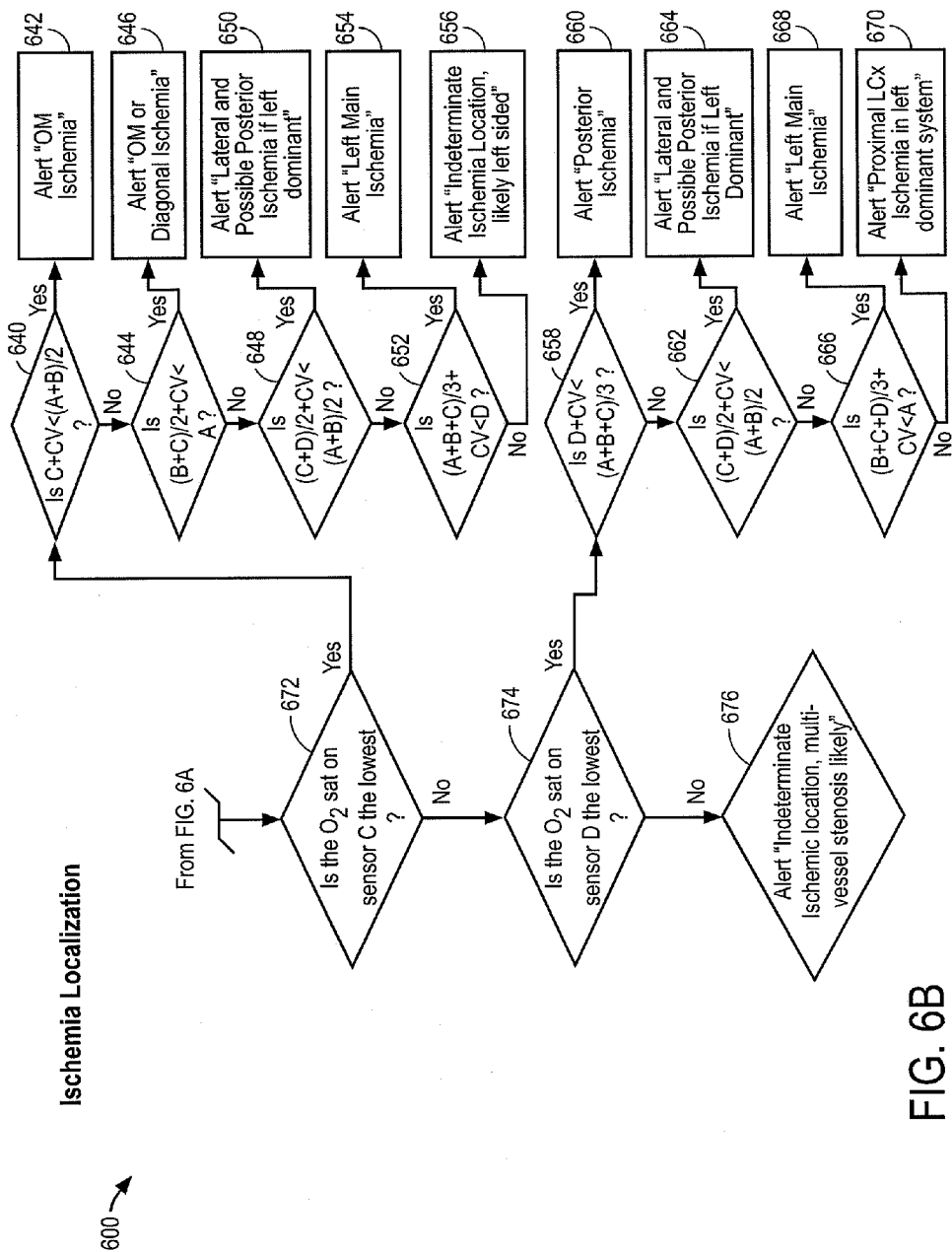

In one embodiment, the device 300 can be used to determine a location of the ischemia. That is, the reading at multiple sensors can be used to determine an approximate location of the ischemia. An exemplary flowchart 600 for localizing ischemia by measuring oxygen saturation is shown in FIGS. 6A and 6B with reference to the placement of sensors in FIG. 3—sensor A in the region of the venous drainage of the distal left anterior descending artery 103, sensor B in the region of the venous drainage distal to the left circumflex artery 105, sensor C in the great cardiac vein 204, and sensor D near the ostium 202. It is to be understood that the sensors can be in other locations and/or that steps other than the exemplary process described in flowchart 600 could be used to determine the location of the ischemia.

At step 602, the oxygen saturation in the coronary sinus is measured at multiple locations by sensors A, B, C, and D continuously. At step 603, it is determined if at least one sensor has measured an oxygen saturation that exceeds the threshold value by having an oxygen saturation that is below the cutoff value, for example has an oxygen saturation that is greater than 5% below from the baseline value (as described above with respect to flowcharts 400 and 500). If there is no sensor exceeding the threshold, then the oxygen saturation can continue to be measured at step 602. If one of the sensors has measured an oxygen saturation that exceeds the threshold, then it can be determined which sensor measures the lowest oxygen saturation (as the lowest oxygen saturation would suggest the greatest blockage).

At step 604, therefore, it can be determined whether sensor A in the region of the venous drainage of the left anterior descending artery has the lowest oxygen saturation. If so, then it can be determined at step 606 whether the oxygen saturation measured with sensor A plus the cutoff variation (CV) is less than the oxygen saturation measured at sensor B. If so, then this would indicate that the primary blockage is near sensor A (as the blockage has extended up to sensor B), and thus, at step 608, it can be determined and alerted that there is possible ischemia in the distal left anterior descending artery. If, on the other hand, the oxygen saturation measured with sensor A plus the cutoff variation is not less than the characteristic measured at B, then it would indicate that the blockage is also near sensor B. Accordingly, at step 610, it can be determined whether the average oxygen saturation at sensors A and B plus CV is less than the average saturation at sensors C and D. If it is, then it can be determined and alerted at step 612 that the blockage is in the proximal left anterior descending artery. On the other hand, if the average oxygen saturation at sensors A and B plus CV is not less than the average saturation at sensors C and D, then it would indicate that the blockage is either more extensive than just the region near sensor A or simply closer to sensor C. Accordingly, it can be determined, at step 614 whether the average saturation at sensors A, B, and C plus CV is less than the saturation at D. If so, then it can be determined and alerted at step 616 that there is likely left main ischemia. If not, then at step 618 an alert can be made that the ischemia is likely left sided, but with an indeterminate location.

If, on the other hand, sensor A does not have the lowest saturation, then it can be determined at step 620 whether sensor B has the lowest oxygen saturation. If so, then it can be determined at step 622 whether the saturation at sensor B plus CV is less than the saturation at A. If so, then it can be determined and alerted that there could be LAD/diagonal ischemia at step 624 (as the ischemia would be near sensor B). If the saturation at sensor B plus CV is not less than A, then it can be determined whether the average of the saturation at A and B plus CV is less than C. If so, then it can be determined and alerted at step 628 that proximal LAD ischemia (i.e. ischemia near sensors A and B) is possible. If not, then at step 630, it can be determined whether the average of the saturation at B and C plus CV is less than the saturation at A. If so, then at step 632, it can be determined and alerted that OM or diagonal ischemia (i.e. ischemia near sensors B and C) is possible. If not, then at step 634, it can be determined whether the average saturation at sensors A, B, and C plus CV is less than D. If so, then at step 636 it can be determined and alerted that left main ischemia is possible. If not, then at step 638, it can be alerted that ischemia is likely left sided, but with an indeterminate location.

If, on the other hand, sensor B does not have the lowest saturation, then it can be determined at step 672 whether C has the lowest saturation. If so, then it can be determined at step 640 whether the saturation at sensor C plus CV is less than the average saturation of sensors A and B. If so, then at step 642, it can be determined and alerted that OM ischemia (near sensor C) is possible. If not, then at step 644, it can be determined whether the average of the saturation at sensors B and C plus CV is less than the saturation at A. If so, then it can be determined and alerted at step 646 that OM or diagonal ischemia is possible. If not, then at step 648 it can be determined whether the average of the saturation at sensors C and D plus CV is less than the average saturation at sensors A and B. If so, then it can be determined and alerted at step 650 that lateral ischemia and posterior ischemia if the patient's heart is left dominant are possible. If not, then at step 652, it can be determined whether the average saturation at sensors A, B, and C plus CV is less than the saturation at D. If so, then it can be determined and alerted at step 654 that left main ischemia is possible. If not, then at step 656, it can be alerted and determined that left-side ischemia is likely with an indeterminate location.

If sensor C does not have the lowest saturation, the nit can be determined at step 674 whether the oxygen saturation at sensor D is the lowest. If so, then it can be determined at step 658 whether the saturation at sensor D plus CV is less than the average saturation at sensors A, B, and C. If so, then at step 660 it can be determined and alerted that posterior ischemia is possible (posterior to or near sensor D). If not, then it can be determined at step 662 whether the average of the saturation at sensors C and D plus CV is less than the average saturation at sensor A and B. If so, then it can be determined and alerted at step 664 that lateral ischemia and possible posterior ischemia if the patient's heart is left dominant are possible. If not, then it can be determined at step 666 whether the average of the saturation at sensors B, C, and D plus CV is less than the saturation at sensor A. If so, then it can be determined and alerted at step 668 that left main ischemia is possible. If not, then it can be determined and alerted at step 670 that proximal LCx ischemia, particularly if the patient's heart is left dominant, is possible.

Finally, if neither A, B, C, or D has the lowest oxygen saturation, then at step 676, it can be determined and alerted that the ischemia location is indeterminate and that multi-vessel stenosis is likely.

Although flowchart 600 is described with respect to measurements of oxygen saturation, any of the characteristics described herein that relate to ischemia could be used to determine the approximate ischemia location in a similar manner.

It is to be understood that the devices described herein need not perform all of the steps of the flowcharts and/or may perform them in a different order. For example, the devices described herein could be used to gather and store data corresponding to coronary blood flow, and that gathered data could then be reviewed later, such as by a doctor, without sounding an alarm as suggested in flowchart 400 or performing a stress test as suggested in flowchart 500. In some embodiments, the gathered data can be compared to a standard baseline and/or to a set threshold rather than using the device to establish a baseline. Further, although flowchart 600 shows the measurement oxygen saturation by sensors A, B, C, and D, it is to be understood that other blood characteristics can be used as well and that other sensor locations are possible.

In one embodiment, the microprocessor 334 in the device 300 is used to carry out some or all of the steps of the flow charts 400, 500, and/or 600. In other embodiments, an external controller can be used to carry out some or all of the steps of the flowcharts 400, 500, and/or 600.

In some embodiments, the heating and/or cooling element can be used to isolate the location of the blockage. By heating or cooling distal aspects of the coronary sinus, the proximal temperature curve will enable calculation of total blood flow drainage through the coronary sinus and relative blood flow through each coronary artery through thermodilution cardiac output calculations. The heating or cooling element can thus advantageously augment the ability of the device to determine and isolate coronary blockage.

Further, it is to be understood that other variations of the device 300 are possible. For example, in some embodiments, one or more of the leads can include one or more radiographic markers that can be used during imaging to place and/or monitor the placement of the device. For example, the radiographic markers can be placed at a set distance relative to the sensors, such as proximate to the sensors, to enable placement of the sensors at the desired locations, e.g., proximate to branches in the coronary sinus.

In some embodiments, the leads 310 can include a drug delivery reservoir for delivering drug to the coronary/myocardial areas. For example, a balloon on the lead can be used to deliver drugs to the coronary artery.

The devices and methods described herein can advantageously be used to detect coronary ischemia (and even ischemia location) without the need for other expensive diagnostic work-up (for example, the patient can avoid having to expend the energy and time required for treadmill testing). The device can be used in patients who would likely already have a need for a pacemaker or defibrillator, thereby reducing the amount of intrusion needed for the patient. Further, because patients with pacemakers and/or implantable cardiac defibrillators generally have their devices checked routinely, the data can be reviewed and/or the device can be used in stress test mode regularly, without additional hassle for the patient, to check for myocardial ischemia. Alternatively, as discussed above, a warning can sound if the measured characteristic has exceeded a threshold value during routine use, thereby allowing for detection of ischemia without a visit to the doctor's office.

Advantageously, the devices and methods described herein can detect physiologically significant progression in coronary artery disease by continuously measuring characteristics that can sense any derangement in the basic metabolic principle of oxygen supply and demand within the myocardium, which is the primary determinant in the natural history of ischemic heart disease. Further, the devices and methods describe herein can permit both absolute evaluation of the coronary arteries, for example by measuring blood flow through use of the heating element and/or thermodilution to determine absolute blood flow and functional evaluation of the coronary arteries, for example by measuring oxygen saturation.

The devices and methods described herein can thus be used to accurately assess for silent myocardial ischemia and potentially prevent a myocardial infarction from occurring.

What is claimed is:

1. A system for detecting myocardial ischemia comprising:
   an implantable device having one or more leads connected thereto;
   at least one electrode on a lead of the device, the electrode configured to stimulate the heart;
   at least two oximetry sensors on one or more leads of the device, the at least two oximetry sensors configured to measure oxygen saturation in a coronary sinus; and
   a microprocessor in the implantable device programmed to:
   run a stress test on the heart by stimulating the heart with the electrode;
   record data obtained from the at least two oximetry sensors during the stress test;
   determine whether there is myocardial ischemia based upon the recorded data; and
   determine a location of the myocardial ischemia based upon a difference in the oxygen saturation measured at the at least two oximetry sensors.

2. The system of claim 1, wherein the microprocessor is configured to determine whether there is myocardial ischemia by determining whether data recorded from the sensor during the stress test has exceeded a threshold value.

3. The system of claim 2, wherein the microprocessor is further configured to establish a baseline from the recorded data and set the threshold value using the baseline.

4. The system of claim 1, further comprising an alarm connected to the implantable device and configured to transmit a warning signal if myocardial ischemia is detected.

5. The system of claim 1, wherein the implantable device is a pacemaker or defibrillator.

6. The system of claim 1, further comprising a heating or cooling element on the lead.

7. A method of detecting myocardial ischemia comprising:
   measuring oxygen saturation of blood in a coronary sinus with at least two oximetry sensors on one or more leads of an implantable device;
   recording data obtained from the sensor in a memory of the implantable device to establish a baseline;
   performing a stress test with the implantable device;
   measuring the oxygen saturation with the sensors during the stress test;
   comparing the oxygen saturation measured during the stress test with the baseline to detect whether there is myocardial ischemia; and
   determining a location of the myocardial ischemia based upon a difference in the oxygen saturation measured at the at least two oximetry sensors.

8. The method of claim 7, wherein performing a stress test comprises pacing the heart with an electrode coupled to the device at a rate of at least 100 beats per minute.

9. The method of claim 7, wherein performing a stress test comprises pacing the heart at a first rate for a set period of time and then, if no ischemia has been detected, increasing the rate of pacing.

10. The method of claim 9, further comprising stopping the stress test if the pacing rate is greater than a predetermined amount and no ischemia has been detected.

11. The method of claim 1, further comprising placing the at least two sensors at predetermined locations in the coronary vessel that are proximate to branches in the vessel.

12. The method of claim 1, wherein the characteristic is temperature, and wherein the method further comprises heating blood in the coronary vessel using a heating or cooling element on the lead and comparing the measured temperature at the at least two sensors.

13. The method of claim 7, the method further comprising implanting the lead in the coronary sinus.

14. The device of claim 1, wherein the at least two oximetry sensors are on a single lead.

15. The method of claim 7, wherein the at least two oximetry sensors are on a single lead.

* * * * *